United States Patent [19]

Fischler et al.

[11] 4,100,195
[45] Jul. 11, 1978

[54] PROCESS FOR PREPARING DIPHENYLAMINE IN THE PRESENCE OF A BORON/FLUORINE COMPOUND AND WATER

[75] Inventors: Hans-Michael Fischler; Dieter Bauer; Hein Quast, all of Krefeld, Germany

[73] Assignee: Bayer Aktiengesellschaft, Leverkusen, Germany

[21] Appl. No.: 822,979

[22] Filed: Aug. 8, 1977

Related U.S. Application Data

[63] Continuation of Ser. No. 679,112, Apr. 22, 1976, abandoned.

[30] Foreign Application Priority Data

May 13, 1975 [DE] Fed. Rep. of Germany ....... 2521293

[51] Int. Cl.$^2$ .............................................. C07C 85/20
[52] U.S. Cl. .................................... 260/576; 252/433; 252/429 R
[58] Field of Search ......................... 260/576; 252/433

[56] References Cited

U.S. PATENT DOCUMENTS

| | | | |
|---|---|---|---|
| 2,135,454 | 11/1938 | McAlevy | 252/433 |
| 2,158,031 | 5/1939 | Loder | 260/338 |
| 2,370,118 | 2/1945 | Axe | 260/683.65 |
| 3,071,619 | 1/1963 | Kehe et al. | 260/576 |

FOREIGN PATENT DOCUMENTS

| | | | |
|---|---|---|---|
| 478,085 | 1/1938 | United Kingdom | 252/433 |
| 1,402,707 | 8/1975 | United Kingdom | 260/576 |

OTHER PUBLICATIONS

Booth et al., "Boron Trifluoride and its Derivatives" (1949).
Sowa et al., "JACS", vol. 59, pp. 1202–1203 (1937).

*Primary Examiner*—Daniel E. Wyman
*Assistant Examiner*—John J. Doll
*Attorney, Agent, or Firm*—Burgess, Dinklage & Sprung

[57] ABSTRACT

Diphenylamine is made by heating aniline under pressure and temperatures of 250°–400° C in the presence of a boron/fluorine compound and water.

10 Claims, 1 Drawing Figure

PROCESS FOR PREPARING DIPHENYLAMINE IN THE PRESENCE OF A BORON/FLUORINE COMPOUND AND WATER

This is a continuation of application Ser. No. 679,112 filed Apr. 22, 1976, now abandoned.

BACKGROUND

This invention relates to a process for the preparation of diphenylamine from aniline in the liquid phase, in the presence of boron/fluorine compounds and water.

A process for the preparation of diphenylamine by heating aniline with small amounts of boron fluoride, or of an aniline/boron fluoride or ammonia/boron fluoride complex, under pressure to temperatures between 250° and 400° C is described in German Published Specification No. 1,116,231. However, with this process the reaction must be carried out with anhydrous aniline and, in addition, recovery of the catalyst involves considerable effort.

Furthermore, a process for the preparation of diphenylamine by heating aniline under elevated pressure in the presence of boron fluoride as the catalyst is known from U.S. Pat. No. 3,071,619 and in the process boron fluoride is preferably employed as ammonium fluoborate. The disadvantage of this process lies in the insolubility of the solid catalyst, that is to say ammonium fluoborate, in the reaction mixture and the metering and separating problems associated therewith.

SUMMARY

It has now been found that the abovementioned disadvantages may be completely avoided and, furthermore, better space-time yields may be obtained with the same amounts of catalyst when, in place of the anhydrous boron/fluorine compounds used hitherto, water-containing mixtures of boron/fluorine compounds are employed as catalysts.

According to the present invention there is provided a process for the preparation of diphenylamine by heating aniline under pressure to temperatures of 250° to 400° C, in the presence of a boron/fluorine compound and water.

DESCRIPTION OF THE DRAWING

The accompanying drawing is a graph comparing the results of Examples 22 - 24 herein.

DESCRIPTION

Figure 1:
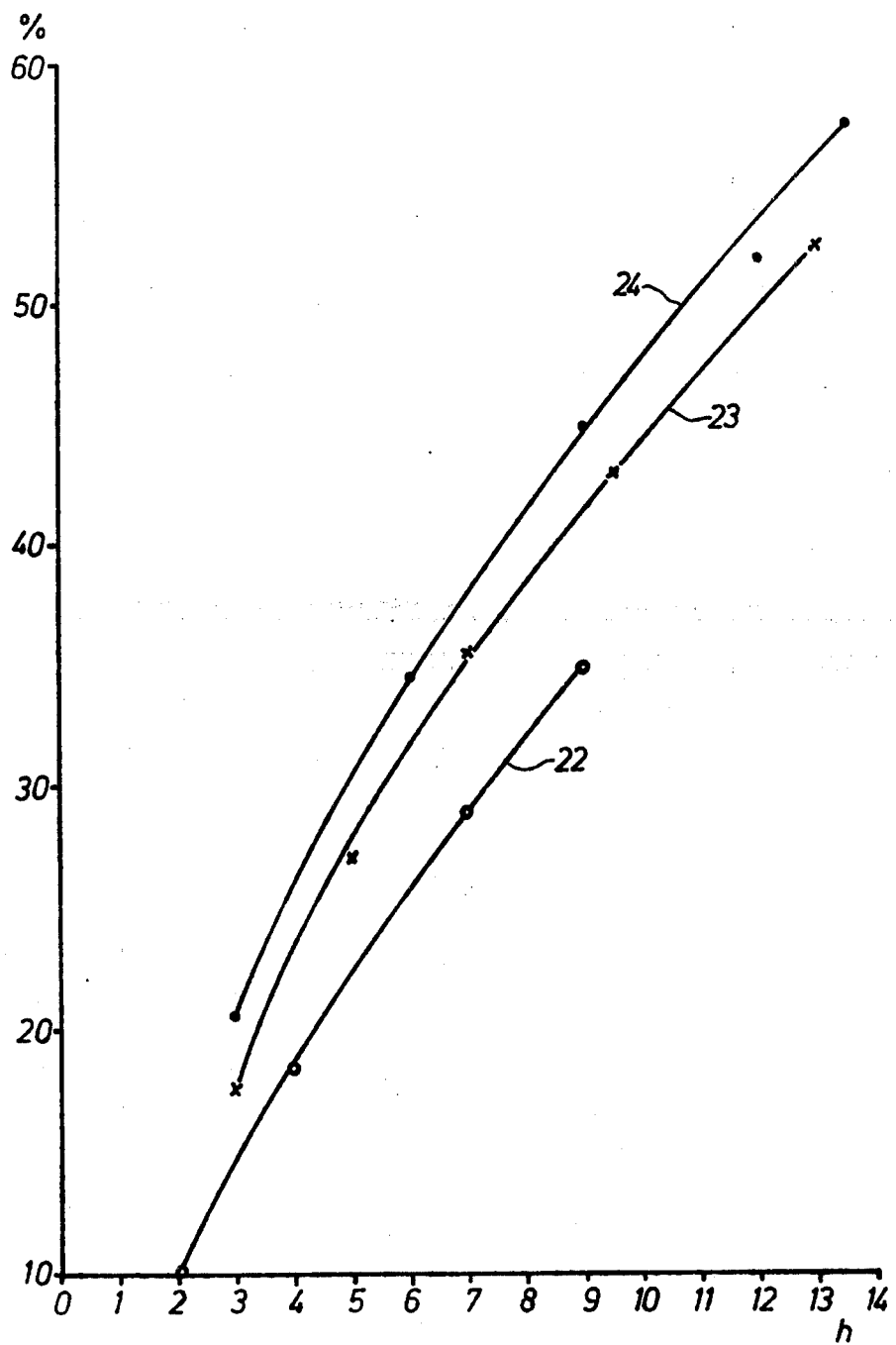

In order to obtain a good space-time yield, the process according to the invention is generally carried out in the customary manner at elevated temperature and elevated pressure, whilst boiling the reaction mixture, and, advantageously, the ammonia gas formed is allowed to escape, at the rate at which it is formed, through a cooled column via a pressure valve and the pressure is thus controlled. Since the reaction is usually carried out at the boiling point of the reaction mixture under the reaction pressure, the pressure and the temperature are interdependent and in some cases are subject to an upper limit imposed by the maximum pressure permissible for the apparatus used or by the expense of appropriate pressure vessels.

In general, therefore, the process according to the invention is carried out in the temperature range between 250° and 400° C under pressures of between 6 and 35 bars; preferably, the reaction is carried out in the temperature range between 300° and 360° C and, when the reaction mixture is at the boil, pressures between 12 and 30 bars are set up when the reaction is carried out at approximately the boiling pressure of the reaction mixture, the composition of which changes during the reaction.

Virtually all boron/fluorine compounds, both in bulk and in the form of their solutions, preferably in water and/or aniline, can be used in the process according to the invention; examples which may be mentioned are gaseous $BF_3$, the known complexes of borontrifluoride with ammonia and organic amines $BF_3.NH_3$, $BF_3.N(CH_3)_2$, $BF_3.N(C_2H_5)_2$ and $BF_3$.aniline, the $BF_3$-hydrates $BF_3.H_2O$ and $BF_3.2H_2O$, $BF_3$-ether complexes like $BF_3.O(CH_3)_2$ and $BF_3.O(C_2H_5)_2$, solid $NH_4BF_4$, commercial solutions of $HBF_4$ or the liquid complex mixtures which are obtained $NH_4F$, or solid $(NH_4)HF_2$ (of Kirk-Othmer, 2nd ed., Vol. 9, p. 558) and the mixtures of boric acid with hydrofluoric acid in aniline.

Only the boron/fluorine complex compounds containing metal cations are not suitable.

The amount of the boron/fluorine compounds used according to the invention is variable within wide limits. Appropriately, 0.1 to 5.0, preferably 0.2 to 3.0, % by weight of the boron/fluorine compound, calculated as $BF_3$ and based on the amount of aniline employed, is used.

When preparing the mixtures of boron/fluorine compounds, according to the invention, it is not necessary to maintain a molar ratio of boron : fluorine of 1 : 3. The ratio can be varied within the limits of 1 : 2 to 1 : 4 without impairing the catalytic activity of the boron/fluorine compound.

In general, 0.1 to 5.0, preferably 0.2 to 4.0, % by weight of water, based on the amount of aniline, is used.

In a particularly advantageous variant of the process according to the invention, the boron/fluorine compound, when it is employed as the catalyst for the first time, is used in the form of a homogeneous mixture, which is obtained by adding anhydrous or aqueous, preferably commercially available 40 or 70 to 75% strength by weight hydrofluoric acid to a suspension of boric acid in aniline, whilst stirring, in a temperature range of, preferably, 50° to 80° C; the addition can be started at room temperature and the heat of reaction used in order to reach and maintain the abovementioned temperature range; any excess heat of reaction must be removed by external cooling.

Of course, with this method of preparation of the boron/fluorine compound, according to the invention, in aniline, the desired amount of water, when this is not already obtained by the water of reaction formed, can not only be introduced via the aqueous hydrofluoric acid solution but can be varied within the indicated limits by additional addition of water.

For this method of preparation, the amount of aniline to be used is subject only to a lower limit, which is given by the fact that the amount of aniline used should be at least such that the boron/fluorine/aniline complex formed remains in solution and that the water which is additionally added if necessary dissolves in the aniline. The amount of aniline necessary for this depends on the corresponding solubilities and on the temperature; it can optionally be calculated from known data or determined easily by a few experiments. Of course, it is also possible to use from the start the amount of aniline corresponding to the amount of catalyst.

The process according to the invention is illustrated below by the reaction equation:

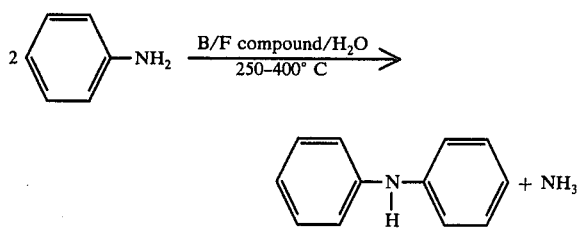

In general, the process according to the invention is carried out in such a way that the boron/fluorine compound, according to the invention, which is used, and water, are added in the chosen amounts to aniline and the reaction mixture is heated to the chosen reaction temperature. As described above, it is also possible to prepare the boron/fluorine compound before the start of the reaction at a lower temperature in some, or in the total amount, of the aniline. Due to the elimination of ammonia during the reaction, in a closed vessel the pressure rises above normal pressure, so that, in order to reach and maintain the chosen reaction pressure, it is necessary only to control the ammonia, which escapes as off-gas, by means of a control valve.

Customary apparatus, for example autoclaves made of carbon steel, which are provided with reflux condensers and off-gas valves for the ammonia gas formed as well as with filling and emtying devices and, if appropriate, stirring devices, can be used for carrying out the process according to the invention. Heating can also be effected in the customary manner, for example by means of a heat exchange medium, directly by combustion gases or electrically. The customary apparatus, for example an autoclave cascade, can also be used for carrying out the process according to the invention continuously. The design of the apparatus is not a factor essential to the invention and can be in accordance with the state of the art. As is known, the elimination of ammonia from 2 mols of aniline, and thus the formation of diphenylamine, proceeds at an adequate rate only until a concentration of about 50 to 55% of diphenylamine is reached in the reaction mixture. Advantageously, therefore, the reaction is then discontinued, the reaction mixture is worked up and unreacted aniline is re-employed in the reaction.

When the reaction has ended, the boron/fluorine compound used as the catalyst can be recovered by extracting the reaction mixture with water. Due to the unavoidable losses of water with the ammonia gas which escapes during the reaction, it is appropriate to add water in an amount which is at least such that the aqueous phase formed is adequate to take up the boron/fluorine compound from the reaction mixture.

It is possible both to employ so much water that the aqueous solution is obtained as the light phase and also to employ a little water, so that the aqueous solution is obtained as the heavy phase. In the former case the aqueous solution of the catalyst complex is of low concentration and in the latter case it is of high concentration.

Advantageously, however, a 2-fold to 4-fold amount by weight of water, based on the amount of the boron/fluorine compound to be extracted, is used for the extraction. An aqueous solution of the boron/fluorine catalyst, which, without hesitation, can be re-employed as such in the reaction and which contains the boron/fluorine compound and water in a suitable ratio, is then obtained.

The extraction of the boron/fluorine compound with water can, of course, also be carried out with any apparatus used industrially for extractions, both discontinuously and continuously and in a single stage or in several stages; for example, extraction columns, separators or mixer-settlers can be used. In this case also the design of the apparatus, which is in accordance with the state of the art, is not an essential feature of the invention.

The technical advance of the process according to the invention is based on the following: compared with the state of the art, less boron/fluorine compound is required. When, for example, 1.0% by weight of dry ammonium fluoborate was used as the sole catalyst, a conversion of 27.5% of the aniline employed was achieved in 7.5 hours, whilst, under the same conditions, the additional use of 2% by weight of water led, in the same time, to a conversion of 37.0%. Conversely, it was necessary, under these conditions, to use only 0.6% by weight of ammonium fluoborate in addition to 2% by weight of water in order to achieve a conversion of 27.5%.

The simpler handling and separation of the aqueous homogeneously liquid catalyst mixtures and the ease of separation thereof after the reaction has ended have already been mentioned above. This is of particular advantage when the process according to the invention is carried out continuously.

In addition, the advantage of the known use of anhydrous boron fluoride and boron fluoride complexes, that is to say the lack of a corrosive effect, is retained in full.

The corrosion characteristics of iron (ST 37) and $V_4A$ steel (material No. 1.4571) used as the construction material was checked over a total running time of 1,520 hours by carrying out several test batches of the production, according to the invention, of diphenylamine. In detail, the following rates of corrosion were obtained, and these vary depending on whether the material came into contact with the liquid phase or mainly with the gas phase present above the latter:

| liquid phase: | ST 37 | 0.07 mm loss/year |
|---|---|---|
|  | $V_4A$ (1.4571) | 0.04 mm loss/year |
| gas phase: | ST 37 | 0.15 mm loss/year |
|  | $V_4A$ (1.4571) | 0.08 mm loss/year |

The measured rates of corrosion are of the same order of magnitude as are known for the production of diphenylamine with anhydrous boron fluoride catalysts.

Diphenylamine is useful as dye intermediate, as raw material for making rubber chemicals, antioxidants and anthelmintic pharmazeuticals and as stabilizer for explosives.

EXAMPLES

An externally electrically heated 5 liter steel autoclave, which was fitted with nozzles for filling and sampling and for measuring the temperature and pressure and with a vertical air-cooled jacketed tube for removing the ammonia formed during the reaction, was used when the examples indicated below were carried out. When carrying out each of the examples, the stream of ammonia was uniformly regulated, by means of a valve, so that the temperature at the end of the jacketed tube did not exceed 130° C and thus entrained and gaseous aniline largely condensed in the cooled jacketed tube and refluxed; losses of aniline were thus virtually avoided.

EXAMPLES 1 TO 8

In each case, the amount of BF₃ and, where appropriate, of H₂O indicated in Table I which follows were added to 3,000 g of aniline and the mixture was heated for the indicated reaction time to a reaction temperature of about 330° C.

When the indicated reaction time had elapsed, the diphenylamine content in the reaction mixture was determined by gas chromatography and density measurement; it is given in % by weight, based on the reaction mixture, in Table I which follows.

Table I

| Ex. | Aniline | BF₃* | H₂O | Reaction time (hours) | DPA content* % |
|---|---|---|---|---|---|
| 1* | 3,000 g | 9.0 g = 0.3% | — | 10 | 24.5 |
| 2 | 3,000 g | 9.0 g = 0.3% | 20 g = 0.66% | 10 | 37.0 |
| 3* | 3,000 g | 12.0 g = 0.4% | — | 10 | 35.5 |
| 4 | 3,000 g | 12.0 g = 0.4% | 30 g = 1% | 10 | 45.0 |
| 5* | 3,000 g | 19.8 g = 0.66% | — | 7.5 | 26.0 |
| 6 | 3,000 g | 19.8 g = 0.66% | 15 g = 0.5% | 7.5 | 37.5 |
| 7 | 3,000 g | 19.8 g = 0.66% | 30 g = 1% | 7.5 | 44.0 |
| 8* | 3,000 g | 39.6 g = 1.32% | — | 7.5 | 46.5 |

*Note:
DPA = diphenylamine.

Because of the greater ease of metering, BF₃ was added in the form of the equivalent amount of the solid BF₃-aniline complex, which was obtained by adding together equimolar amounts of BF₃ gas and aniline in ether and subsequently filtering off the complex which had precipitated.

Examples 1, 3, 5 and 8 are comparison examples.

EXAMPLE 9

A mixture of 3,000 g (32.2 mols) of aniline, 14.5 g of 73% strength by weight hydrofluoric acid (0.528 mol of HF) and 10.9 g of boric acid (0.176 mol of B), corresponding to a content of 0.4% by weight of BF₃, based on aniline, and 0.45% by weight of water was heated as described above to about 330° C for 10 hours. The pressure generated initially was about 23 bars and this was let down uniformly in the course of the reaction until, at the end, it was 14.8 bars.

The weight of the reaction mixture was 2,890 g, with an analytically determined content of 42.5% of diphenylamine; the aniline conversion was 45.2%).

The reaction mixture was extracted by shaking with twice 300 ml of water and the aqueous phases were combined; by careful evaporation in vacuo, 51 g of a 30% strength by weight fluoborate salt solution were obtained.

The organic phase was washed with sodium carbonate solution until neutral and was then subjected to fractional distillation; 1,155 g of diphenylamine with a boiling point of 159° C/10 mm Hg and a solidification point of 52.7° C were obtained (94% of theory, based on converted aniline).

EXAMPLE 10

The fluoborate salt solution obtained according to Example 9 was added to 3,000 g of aniline and the mixture was heated, as described above, to about 330° C for 10 hours. After this time, the reaction mixture contained 50.5% by weight of diphenylamine.

EXAMPLE 11

200 g of 73% strength by weight aqueous hydrofluoric acid were added to a mixture of 410 g of aniline and 120 g of boric acid, whilst stirring and cooling, at such a rate that the temperature did not rise above 75° C, and the mixture was stirred until a homogeneous mixture had formed.

In each case 80 g of this mixture were added to, in each case, 2,950 g of aniline and the mixture was heated to about 330° C in the apparatus described above.

In the first case, the initial pressure generated was 22.1 bars and this was let down uniformly to 11.1 bars during a reaction time of 5 hours. After this time, the reaction mixture contained 40.7% by weight of diphenylamine.

In the second experiment, the reaction pressure initially generated was 22.5 bars and this was let down uniformly to 10.2 bars over a reaction time of 7.5 hours. After this time, the reaction mixture contained 53.3% by weight of diphenylamine.

EXAMPLES 12 TO 15

47.0 g of 35% strength by weight aqueous fluoboric acid were added to, in each case, 3,000 g of aniline and the mixture was heated to about 330° C for various times in the apparatus described above.

Table II which follows gives the reaction time and the analytically determined content of diphenylamine (DPA) in the reaction mixture at the end of the reaction time.

Table II

| Ex. | Reaction time (hours) | DPA content (% by weight) |
|---|---|---|
| 12 | 1.5 | 15.5 |
| 13 | 2.5 | 22.3 |
| 14 | 4.5 | 35.5 |
| 15 | 5.5 | 46.0 |

EXAMPLES 16 AND 17 (COMPARISON EXAMPLES)

In each case 47.0 g of aqueous fluoboric acid were mixed with, in each case, 100 g of aniline and the water was distilled from the mixture in vacuo. In each case 17.0 g of anhydrous HBF₄ in aniline were thus obtained and, after adding further aniline until the total amount was 3,000 g, the mixture was heated to about 330° C for various times in the apparatus described above. Table III which follows gives the reaction times and the diphenylamine (DPA) content in the reaction mixture at the end of the reaction time.

Table III

| Ex. | Reaction time (hours) | DPA content (% by weight) |
|---|---|---|
| 16 | 6 | 27.3 |
| 17 | 7.5 | 31.0 |

EXAMPLE 18

3,000 g of aniline, together with 30.0 g of finely powdered ammonium fluoborate and 30 g of water, were heated to about 330° C for 7.5 hours in the apparatus described above. At the end of the reaction time, the diphenylamine content in the reaction mixture was 40.5% by weight.

EXAMPLE 19 (COMPARISON EXAMPLE)

3,000 g of aniline, together with 30.0 g of finely powdered ammonium fluoborate, were heated to about 330° C for 7.5 hours in the apparatus described above. At the end of the reaction time, the diphenylamine content in the reaction mixture was 30.0% by weight.

EXAMPLE 20

3,000 g of aniline, together with 39.6 g (1.32% by weight) of boron trifluoride (added in the form of 95.5 g of aniline/$BF_3$ complex) and 30 g (1.0% by weight) of water, were heated to about 310° C for 9 hours, whilst stirring, in the apparatus described above. By controlling the let-down valve, the ammonia formed was released at such a rate that the pressure fell from an initial value of 16.8 bars down to 14.5 bars towards the end of the reaction time. The analytically determined diphenylamine content was then 38.5% by weight.

EXAMPLE 21

3,000 g of aniline, 9.0 g (0.3% by weight) of boron trifluoride (added as 21.5 g of aniline/$BF_3$ complex) and 10.0 g (0.33% by weight) of water were heated to about 350° C for 7 hours, whilst stirring, in the apparatus described above. The pressure initially generated was 23.3 bars and this was let down uniformly to 18.0 bars during the reaction time. After this time, the reaction mixture contained 41.5% by weight of diphenylamine.

EXAMPLE 22 (COMPARISON EXAMPLE)

13.0 kg of aniline, to which 100 g (0.77% by weight) of dry, finely powdered ammonium fluoborate had been added, were heated to about 330° C, whilst stirring, in a 20 liter autoclave, which can be heated electrically and which is fitted with a stirrer, a thermometer, a pressure gauge and sampling branches and with a column attachment with a cooling device and an off-gas valve. By regulating the let-down valve, the stream of ammonia was so adjusted that the reaction pressure fell from 14.8 bars at the start of the reaction down to 11.9 bars at the end of the reaction time. Samples were taken at the intervals indicated in Table IV which follows and the diphenylamine content was determined.

Table IV

| Time (hours) | DPA content (% by weight) |
|---|---|
| 0 | — |
| 2 | 10.0 |
| 4 | 18.5 |
| 7 | 29.0 |
| 9 | 35.0 |

EXAMPLE 23

13.0 kg of aniline, to which 100 g (0.77% by weight) of dry, finely powdered ammonium fluoborate and 50 ml (0.38% by weight) of water had been added, were heated to about 330° C, whilst stirring, in the apparatus described in Example 22. By regulating the let-down valve, the ammonia formed was released at such a rate that the pressure fell from 15.3 bars at the start of the reaction down to 9.0 bars at the end of the reaction time. Samples were taken at certain intervals and the diphenylamine content in the reaction mixture was determined analytically. The corresponding values are summarised in Table V.

Table V

| Time (Hours) | DPA content (% by weight) |
|---|---|
| 0 | — |
| 3 | 17.5 |
| 5 | 27.0 |
| 7.5 | 35.5 |
| 10.5 | 43.0 |
| 13 | 52.5 |

EXAMPLE 24

13.0 kg of aniline, to which 117 g of 73% strength by weight hydrofluoric acid, 86 g of boric acid and 24 g of water had been added, were heated to about 330° C, whilst stirring, in the apparatus described in Example 22; the addition corresponded to 95 g (= 1 mol %) of $BF_3$ and 130 g (= 1% by weight) of $H_2O$. By regulating the let-down valve, the ammonia formed was let down at such a rate that the pressure in the autoclave fell from 19.0 bars at the start of the reaction down to 10.8 bars at the end of the reaction time. Samples were taken at certain intervals and the diphenylamine content of the reaction mixture was determined analytically. The corresponding values are summarised in Table VI which follows.

Table VI

| Time (hours) | DPA content (% by weight) |
|---|---|
| 0 | — |
| 3 | 20.5 |
| 6 | 34.5 |
| 9 | 45.0 |
| 12 | 52.0 |
| 13.5 | 57.5 |

For illustration, the comparable results from Examples 22, 23 and 24 are plotted as a graph in FIG. 1.

EXAMPLE 25 (IN THIS EXAMPLE "PARTS" ARE PARTS BY WEIGHT).

Analogously to Example 11, a homogeneous catalyst mixture is prepared by mixing 200 parts of 73% strength by weight aqueous hydrofluoric acid and 120 parts of solid boric acid in 400 parts of aniline at a maximum of 75° C; according to calculation, the mixture then contains 163.5 parts of the boron/fluorine compound with a molar ratio of boron to fluorine of 1 : 3.57 and 156 parts of water.

For an autoclave batch, this mixture is added to the aniline employed in an amount such that the concentration of the boron/fluorine compound is 0.78% by weight and the concentration of water is 0,74% by weight, based on the amount of aniline employed.

The mixture is then heated, as described above, to 330° to 350° C, the ammonia formed being released as a gas, and the reaction is discontinued after about 55% by weight of the aniline employed has been converted to diphenylamine. The pressure is then about 9.8 bars and the diphenylamine content in the reaction mixture is about 49.5% by weight.

The contents of the autoclave are let down, via a cooler, into a receiver and extracted, at about 70° to 80° C, with an aqueous extraction solution from a preceding batch (obtained as described below) and fresh water in a ratio of 100 : 10 : 1.

The mixture from the extraction then separates into a light crude oil phase containing less than 0.1% by weight of the boron/fluorine compound and a heavier aqueous phase containing about 23% by weight of boron/fluorine compound, the latter being the socalled extraction solution.

The crude oil phase is extracted, for neutralisation, by shaking with 10% strength by weight aqueous sodium carbonate solution and then, by fractional distillation, separated into diphenylamine and aniline, which is re-employed for the reaction. This gives diphenylamine with a solidification point of 52.8° C in a yield of 96% of theory, based on converted aniline.

EXAMPLE 26

For an autoclave batch, the aqueous extraction solution, obtained as described in Example 25, is added, as the catalyst, to the aniline employed in an amount such that the content of the boron/fluorine compound in the reaction mixture is 0.6% by weight and the water content is about 2% by weight, in each case based on the aniline employed. The mixture is heated, as described above, to 330° – 350° C, the ammonia formed being released as a gas, and the reaction is discontinued after about 55% by weight of the aniline has been converted to diphenylamine.

The contents of the autoclave are then let down, as described in Example 25, via a cooler into a receiver and extracted with aqueous extraction solution and fresh water. Further working up is also carried out as described in Example 25. This gives a diphenylamine of the same quality, in a comparable yield.

What is claimed is:

1. Process for producing diphenylamine which comprises heating aniline under pressure to temperatures of 250° to 400° C in the presence of a boron/fluorine compound devoid of metal cations and water in an amount of 0.1 to 5.0% by weight, based on the weight of aniline used.

2. Process of claim 1 carried out under a pressure between 6 and 35 bars.

3. Process of claim 1 carried out at the boiling point of the reaction mixture at a temperature between 300 and 360° C. and at pressures between 12 and 30 bars.

4. Process of claim 1 wherein the boron/fluorine compound is present in an amount of 0.1 to 5.0% by weight, calculated as $BF_3$ and based on the weight of aniline used.

5. Process of claim 4 wherein 0.2 to 3.0% by weight of the boron/fluorine compound, calculated as $BF_3$ and based on the weight of aniline used, is used.

6. Process of claim 1 wherein water is used in an amount of 0.2 to 4.0% by weight, based on the weight of aniline used.

7. Process of claim 1 wherein the boron/fluorine compound is boron trifluoride, ammonium fluoborate or anilinium fluoborate.

8. Process of claim 1 wherein a mixture of hydrofluoride with boric acid or boron trioxide in a molar ratio of boron : fluorine of between 1 : 2 and 1 : 4 is used as the boron/fluoride compound.

9. Process of claim 7 wherein anhydrous or aqueous 40, or 70 to 75% by weight strength by weight hydrofluoric acid is added with stirring to a suspension of boric acid in aniline at a temperature range of 50 to 80° C.

10. Process of claim 1 wherein the boron/fluorine compound is separated off from the reaction mixture when the reaction has ended by extracting with water and the extract thus obtained is re-employed in a further reaction as claimed in claim 1 as the mixture of boron/fluorine compound and water.

* * * * *